United States Patent
Hammer

(10) Patent No.: US 8,297,585 B2
(45) Date of Patent: Oct. 30, 2012

(54) LOAD SUSPENSION STAND AND MICROSCOPY SYSTEM

(75) Inventor: Hermann Hammer, Hemmental (CH)

(73) Assignee: Carl Zeiss Meditec AG, Jena (DE)

( * ) Notice: Subject to any disclaimer, the term of this patent is extended or adjusted under 35 U.S.C. 154(b) by 565 days.

(21) Appl. No.: 12/629,830

(22) Filed: Dec. 2, 2009

(65) Prior Publication Data

US 2010/0142039 A1   Jun. 10, 2010

(30) Foreign Application Priority Data

Dec. 5, 2008   (DE) .................... 10 2008 060 725

(51) Int. Cl.
   *F16M 13/00* (2006.01)
(52) U.S. Cl. ........................... 248/592; 248/580
(58) Field of Classification Search .................. 359/368, 359/372–378, 382; 248/580, 583, 592–594, 248/608, 609, 637–669
See application file for complete search history.

(56) References Cited

U.S. PATENT DOCUMENTS

| | | | |
|---|---|---|---|
| 3,848,473 A | 11/1974 | Diepeveen | |
| 5,492,296 A | 2/1996 | Biber | |
| 6,199,812 B1 | 3/2001 | Schuepbach | |
| 6,254,046 B1 | 7/2001 | Biber | |
| 6,523,796 B2 | 2/2003 | Abramowsky et al. | |
| 6,708,936 B2 | 3/2004 | Metelski | |
| 2003/0094549 A1 | 5/2003 | Gaertner et al. | |
| 2003/0226458 A1 | 12/2003 | Becker et al. | |
| 2007/0012853 A1 | 1/2007 | Strauss et al. | |
| 2008/0237413 A1 | 10/2008 | Hammer | |
| 2009/0218456 A1* | 9/2009 | Metelski | 248/157 |

FOREIGN PATENT DOCUMENTS

| | | |
|---|---|---|
| DE | 42 31 516 C2 | 3/1994 |
| DE | 42 45 034 C2 | 3/1994 |
| EP | 0 781 529 A1 | 7/1997 |
| EP | 0 999 400 A1 | 5/2000 |
| EP | 0 628 290 B1 | 3/2001 |
| EP | 1 205 703 B1 | 6/2006 |
| EP | 1 312 850 B1 | 11/2006 |
| WO | WO 2007/054327 A1 | 5/2007 |

OTHER PUBLICATIONS

European Search Report and Search Opinion of EP Patent Application No. 09015085.5, mailed Mar. 9, 2010, 5 pages total.

* cited by examiner

*Primary Examiner* — Alessandro Amari
(74) *Attorney, Agent, or Firm* — Potomac Patent Group PLLC

(57) ABSTRACT

A load suspension stand includes a first stand member, a second stand member, a joint pivotably connecting the first with the second stand member, a cam plate rotatably fixed to the first stand member, a load transmission lever, an abutment pivotably supporting the load transmission lever at the second stand member, a load reservoir, acting on the second stand member and on the load transmission lever in order to exert a force $F_1$ on the cam plate by means of the load transmission lever, and a drive for displacing the abutment relative to the load transmission lever.

16 Claims, 3 Drawing Sheets

LOAD SUSPENSION STAND AND MICROSCOPY SYSTEM

CROSS-REFERENCES TO RELATED APPLICATIONS

The present application claims priority to German Patent Application No. 10 2008 060 725.8, filed Dec. 5, 2008, entitled "Load Suspension Stand and Microscopy System," the contents of which is hereby incorporated by reference in its entirety.

BACKGROUND OF THE INVENTION

A conventional stand comprises a plurality of components or stand members articulating in pairs, whereby a base stand member is supported by an object like, for instance, a flooring or a wall, and a load is suspended by a final stand member. By shifting the stand members relative to each other using the links joining them, it is possible to shift the load with respect to the object.

One example for such a stand is represented by a stand of a microscopy system carrying a load in the form of a microscopy optic. Such a microscopy system can be used for surgical interventions, whereby the microscopy optic is suspended by the stand such that a surgeon can shift it relative to a patient practically without exerting any force, i.e. by applying only minor actuating forces. This requires that the torsional moments exerted on the stand members by the weight of the microscopy optic and the weight of the stand members themselves are, as far as possible, compensated by the stand in all possible swiveling positions of the stand members relative to each other. The stand should further be adapted to support different microscopy optics differing from each other with respect to its weight and its center of mass position. Attaching additional components like a camera or additional eyepieces may, for example, modify the weight and the center of mass of a microscopy optic. To allow a compensation of the torsional moments exerted on the stand members independent of the swiveling positions, the stand has to be adjusted to such modifications.

Examples of such stands are, for instance, known from DE 42 45 034 C2, DE 42 31 516 C2, EP 1 205 703 B1, EP 1 312 850 B1, U.S. Pat. No. 6,523,796 B2, and WO 2007/054327 A1.

It has been found that conventional stands are inadequate for an adaptation to modified load situations practically independent of the swiveling positions.

SUMMARY OF THE INVENTION

The present invention has been accomplished taking the above problems into consideration.

According to embodiments of the present invention, a load suspension stand provides possibilities for an adaptation to different load situations.

According to further embodiments of the present invention, a microscopy system provides options for modifying a microscopy optic.

According to embodiments, a load suspension stand comprises at least a first component, a second component, a swivel joint linking the first to the second component, and a structure for providing a torsional moment at the joint between the two components. According to embodiments of the present invention, the structure is configured such that the torsional moment provided is modified subject to the swiveling position of the two components with respect to each other.

According to embodiments, the structure is further configured to enable a modification of the characteristic with which the torsional moment provided varies subject to the swiveling position using a drive. The drive may comprise an actuator, such as a motor. The drive may be configured for manual operation and comprise a manually operable rotary knob for that purpose.

According to embodiments, the structure comprises a cam plate rotatably fixed to the first component, and a load transmission lever being supported by the second component and configured to exert a force onto the cam plate. The force acting on the cam plate results in a torsional moment between the two components, whereby it is possible to adjust a desired characteristic of the torsional moment subject to the swiveling position of the two components relative to each other by a suitable configuration of the cam plate.

According to an embodiment, the structure for providing the torsional moment comprises a cam plate being rotatably fixed to the first component of the stand, a load transmission lever, an abutment for a swiveling support of the load transmission lever on the second component of the stand, and a load reservoir acting on the second component and on the load transmission lever, in order to have the load transmission lever exert a force on the cam plate.

According to embodiments of this, the load reservoir comprises a spring, like, for instance, a helical spring, a leaf spring or a gas pressure spring. In order to provide the required load, the spring can be biased in a compressed or in an expanded way.

According to embodiments, the abutment for a swiveling support of the load transmission lever on the second component can be shifted, relative to the load transmission lever, by a drive enabling a modification of the position on the load transmission lever effective for supporting the load transmission lever relative to the second component. This allows modification of the lever action for transmitting the load provided by the load reservoir to the load transmission lever, which results in a modification of the force induced from the load provided by the load reservoir that is acting on the cam plate.

According to embodiments herein, the load transmission lever can exert the force directly onto the cam plate, whereby the load transmission lever may provide options for reducing the friction force between the load transmission lever and the cam plate. These options may, for instance, comprise a roller being rotatably mounted on the load transmission lever or a provision of friction reducing surfaces on the load transmission lever, like, for instance, sliding faces of synthetic material.

According to further embodiments, the load is transmitted indirectly from the load transmission lever to the cam plate by disposing, for instance, a further swiveling intermediate lever in the line of force from the load transmission lever to the cam plate.

According to embodiments, the force transmitted from the load transmission lever onto the cam plate acts on a periphery of the cam plate. The cam plate is then configured such that a distance or a radius of the cam plate between its center and its periphery varies in the circumferential direction around the cam plate. According to alternative embodiments herein, the cam plate may further provide an inside circumferential surface on which a force directed radially outwards from the centre of the cam plate acts to generate the required swiveling position dependent torsional moment.

According to embodiments, the abutment supporting the load transmission lever comprises a roller having the load transmission lever abutted against its outside periphery.

According to an embodiment herein, the drive comprises a slide being displaced relative to the second component and being also abutted against the outer periphery of the roller.

According to embodiments, the roller can be provided with cogs on its outer periphery and both the slide and the load transmission lever may be configured with a cog rail for engaging with the cogs of the roller.

According to further embodiments, a microscopy system is provided comprising a stand according to the previously described embodiments and a load formed by a microscope.

BRIEF DESCRIPTION OF THE DRAWINGS

The forgoing as well as other advantageous features of the invention will be more apparent from the following detailed description of exemplary embodiments of the invention with reference to the accompanying drawings, wherein.

DETAILED DESCRIPTION OF THE INVENTION

Figure 1:
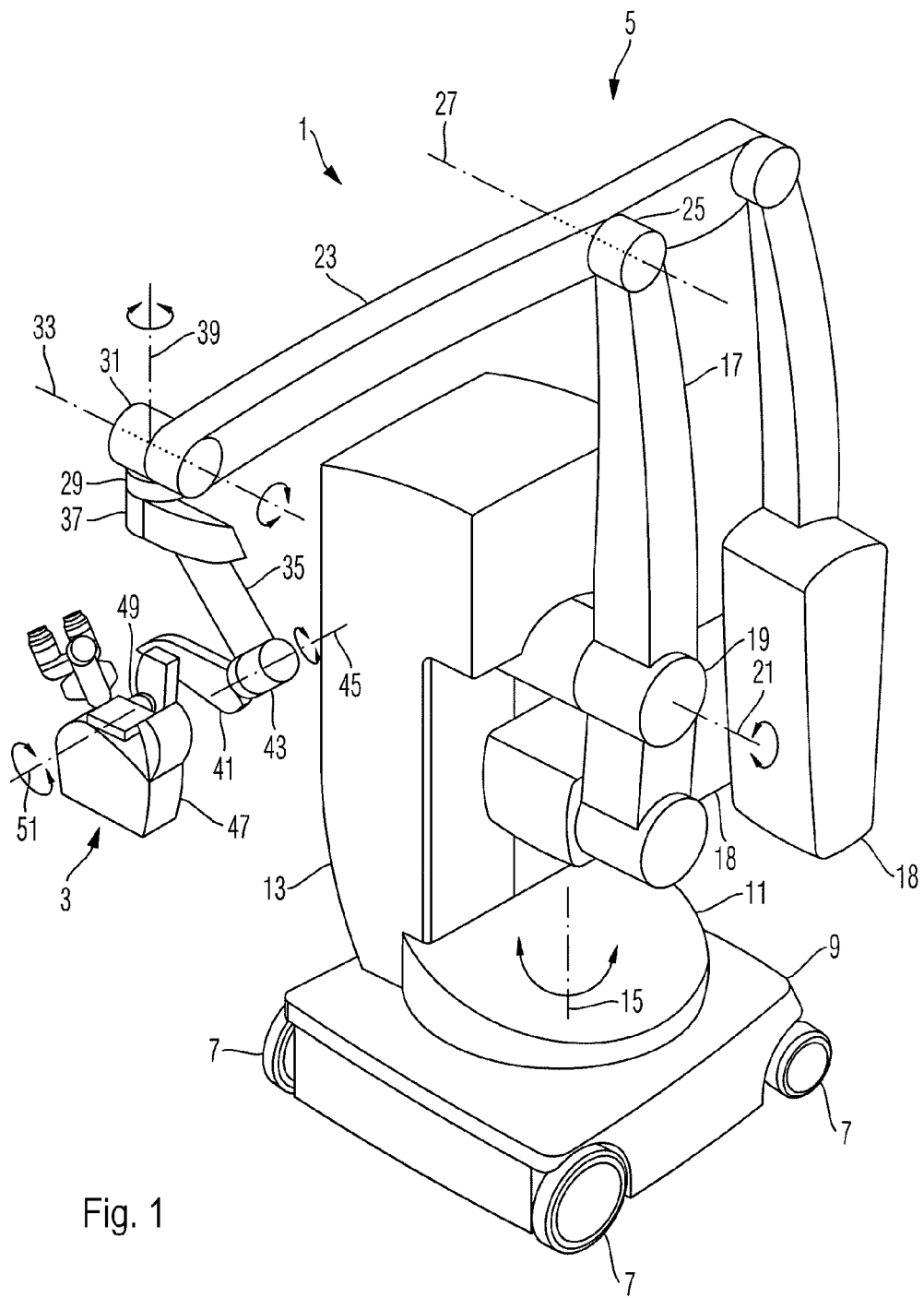
FIG. 1 shows a schematic representation of an embodiment a microscopy system.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

Embodiments of a stand and of a microscopy system comprising a stand are explained below in relation to FIGS. 1 to 3.

A microscopy system 1 as shown schematically in a perspective view in FIG. 1 comprises a microscope 3 mounted on a stand 5. The stand 5 comprises a base 9 provided with wheels 7 to form a base portion of the stand. The base 9 supports a stand member 13 by means of a swivel joint 11 so that the stand member 13 can be pivoted around a pivoting axis 15 extending vertically into space. A further stand member 17 is mounted on the stand member 13 by means of a joint 19 such that it can be swiveled around a horizontal swiveling axis 21. A further stand member 23 is in turn mounted on the stand member 17 by means of a joint 25 so that it can be pivoted around a horizontal pivoting axis 27. A further stand member 29 is in turn mounted on the stand member 23 by means of a joint 31 so that it can be pivoted around a horizontal pivot axis 33. The stand member 29 in turn supports a stand member 35 by means of a joint 37 so that it can be pivoted around a pivot axis 39. A further stand member 41 is in turn articulated to the stand member 35 by means of a joint 43 so that it can be pivoted around a pivot axis 45, and finally a chassis 47 of the microscope is articulated to the stand member 41 serving as the final stand member of the stand 5 by means of a joint 49 so that it can be pivoted around a pivot axis 51. This allows a shifting of the microscope 3 within an available space and an alignment of its orientation in space by swiveling the stand members around the pivot axes.

Two counterweights 18 of the stand 5 are configured to substantially balance the microscope 3 with respect to the swiveling axes 21 and 27, so that a user only has to overcome the residual friction force when swiveling the stand around these axes. Also for swiveling around a vertically aligned pivot axis 15, a user only has to overcome the residual friction force.

The weight of the microscopy optic 3 and the weight of the stand member 41 generate a torsional moment around the swiveling axis 45 that acts on the stand member 35 via joint 43. The torsional moment depends on a swiveling position between the two stand members 35 and 41. A structure, which is explained below in more detail with respect to FIGS. 2 and 3, for compensating for this torsional moment is provided on the stand members 35 and 41.

The two stand members 35 and 41 can be swiveled relative to each other around the pivot axis 45, with the corresponding joint comprising a shaft 51 aligned coaxially to the axis 45 and rotatably fixed to the stand member 35 and pivot-mounted with respect to the stand member 41. Limbs 53 and 54 arranged with a clearance between them and forming part of a U-profile 55 are interspersed with a shaft 51. Stand member 41 is fixed to limb 54 of the U-profile 55, and the U-profile 55 comprises a base plate 56 from which the two limbs 53 and 54 protrude in a perpendicular direction. A cam plate is located in the centre between the two limbs 53 and 54 and affixed to the shaft 51 in a rotationally fixed manner. The cam plate 57 has an outside circumferential surface 58 which distance r to the pivot axis 45 varies in the circumferential direction. In FIG. 3 two distances $r_1$ and $r_2$ are shown as an example for different circumferential directions, whereby the directions of the two distances differ by an angle $\alpha$ of more than 20°, and whereby the ratio of $r_2$ to $r_1$ is more than 1.1.

A roller 61 abuts against the outer periphery 58 of the cam plate 57 with a force $F_1$ such that, because of the configuration of the circumferential surface 58, a torsional moment D acts on the shaft 51 around the axis 45. The roller 61 is mounted rotatably around an axis 67 by means of a shaft 66 and between a pair of intermediate levers 63 and 64. The two intermediate levers 63 and 64 can in turn be pivoted around a pivot axis 69 by means of a shaft 70 mounted on the limbs 53 and 54, whereby the shaft 70 is on both sides fixed to the limbs 53 and 54 of the U-profile 55. The two intermediate levers 63 and 64 jointly carry a pin 71 extending in parallel to the pivot axis 69 between the two intermediate levers 63 and 64. A load transmission lever 73, abutted against a slide 77 by means of a roller 75 serving as an abutment, pushes against the pin 71 with a force $F_2$. A pin 79 further pushes against the load transmission lever 73 with a force $F_3$. The force $F_3$ is provided by a spring 81, which abuts against a cover plate 83 fixedly attached to the limbs 53 and 54 of the U-profile 55, and against a spring receptacle 85 coupled to pin 79. The load transmission lever 73 transforms the force $F_3$ provided by spring 81 in to force $F_2$, mainly in the ratio of the lengths $l_1$ to $l_2$, with length $l_1$ corresponding to the distance between pin 79 and the position at which the load transmission lever 73 abuts against the roller 75, and with length $l_2$ corresponding to the distance between pin 71 and the position at which the load transmission lever 73 abuts against roller 75. Intermediate lever 63 in turn translates the force $F_2$ into force $F_1$ pushing against the periphery 58 of the cam plate 51 and according to the ratio of the lengths $l_3$ and $l_4$, whereby length $l_3$ corresponds to the distance between pin 71 and the pivot axis 69 of the intermediate lever 73, and the length $l_4$ corresponds to the distance between the pivot axis 69 and the rotary axis 67 of roller 61.

Slide 77 abuts against the base 56 of the U-profile 55 by means of rollers 89 accommodated in a cage 87 such that the slide 77 can be shifted back and forth along a direction 91 and such that the forces $F_3$ and $F_2$ exerted by roller 75 on slide 77 are transferred by the rollers 89 onto the U-profile 55.

A drive 93 is provided for displacing the slide 77 in direction 91, the drive comprising a motor 95 with a cog 97 mounted on its driven shaft 96 engaging into a cog wheel 98 for driving a shaft 99 mounted in a bearing block 101. The shaft 99 extends into a recess 103 formed in slide 77. Recess 103 is provided with a female thread engaging with a male thread 105 provided on shaft 99 for transforming a rotational movement of shaft 99 in a linear displacement of a slide 77 along direction 91. The displacement of slide 77 along direction 91 results in a rotation of the roller 75 around its axis, thereby displacing it relative to the load transmission lever 73. By displacing the roller 75 relative to the load transmission lever 73, both lengths $l_1$ and $l_2$ vary and thus also the ratio with which force $F_3$ provided by spring 81 is transmitted into force $F_2$, which is in turn transmitted by intermediate levers 63 and 64 into force $F_1$ acting on cam plate 57. Force $F_1$ can therefore be characterized by:

$$F_1 = \frac{l_3}{l_4} \times \frac{l_1}{l_2} \times c \times \Delta S,$$

whereby c represents the spring rate of spring 81, and $\Delta S$ represents the length of the biased springs 81.

Since the relation $l_1$ to $l_2$, as well as the spring rate c of the spring, are factors in the above equation, the roller or abutment 75, the slide 77 and its drive 93 thus combine to form a drive for varying the effective spring rate of spring 81. The product $c \times l_1/l_2$ can therefore be interpreted as the spring rate of spring 81 effective at the periphery 58 of cam plate 57. An operation of motor 83 therefore results in a variation of the effective spring rate, which could otherwise only be achieved by replacing spring 81 with a stronger or weaker spring.

The structure explained with reference to FIGS. 2 and 3 can therefore be used effectively for operatively compensating the torsional moments generated by microscopy optic 3 and stand member 41 which acts on the pivot axis 45. The structure can in particular be used to compensate for variations of the microscopy optics 3 centre of mass using motor 95.

For achieving a precise displacement of roller 75 relative to the load transmission lever 73, roller 75 is formed by a cog wheel with cogs 105 formed at its periphery, whereby the slide 77 and the load transmission lever 73 comprise corresponding cog rails with cogs 106 and 107 adapted to engage with cog wheel 75.

In the embodiment described above, the load transmission lever 73 transmits the force provided by springs 81 first to the intermediate levers 63 and 64, which eventually transmit the force to the cam plate 57. It is, however, possible to omit the intermediate levers so that the load transmission lever 73 transmits the force directly to the cam plate.

Figure 2:
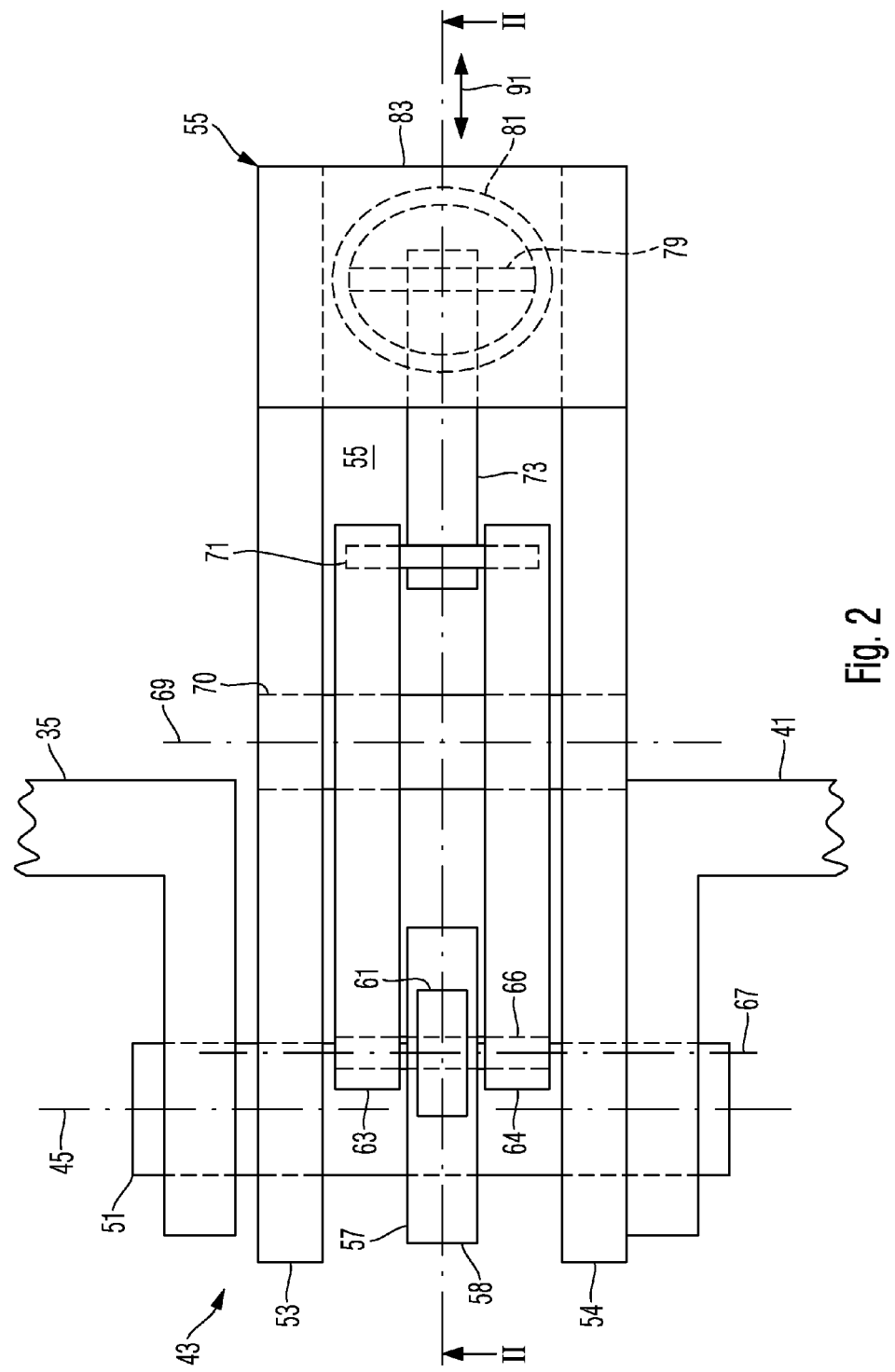
FIG. 2 shows an elevational view of a portion of an embodiment of a stand.
Figure 3:
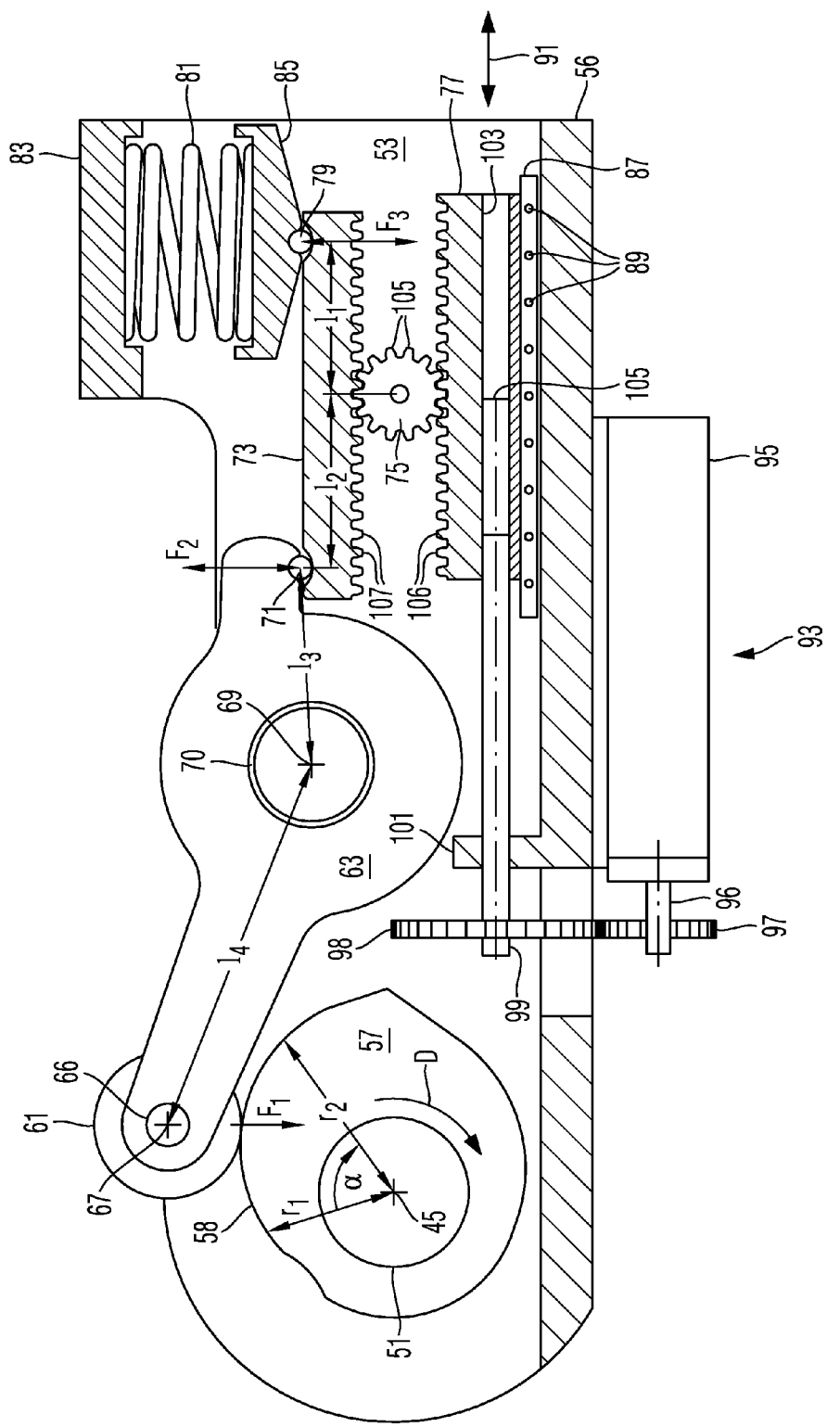
FIG. 3 shows a sectional view of the portion of the stand shown in FIG. 2 along the section line II-II shown in FIG. 2.

The structure for providing a variable torsional moment as explained with reference to FIGS. 2 and 3 is provided between the stand members 35 and 41 of a microscopy system according to an exemplary embodiment as explained with reference to FIG. 1. However, it is appreciated that a respective structure can also be provided between other stand members.

The present invention has been described by way of exemplary embodiments to which it is not limited. Variations and modifications will occur to those skilled in the art without departing from the scope of the present invention as recited in the appended claims and equivalents thereof.

What is claimed is:

1. A load suspension stand comprising:
a first stand member;
a second stand member;
a joint pivotably linking the first stand member to the second stand member;
a cam plate rotatably fixed to the first stand member,
a load transmission lever;
an abutment adapted to pivotably support the load transmission lever at the second stand member;
a load reservoir acting on the second stand member and on the load transmission lever in order to exert a force on the cam plate via the load transmission lever; and
a drive adapted to displace the abutment relative to the load transmission lever.

2. The stand according to claim 1, further comprising an intermediate lever being pivotably mounted on the second stand member, whereby the load transmission lever transmits the force to the cam plate via the intermediate lever.

3. The stand according to claim 1, wherein the abutment comprises a roller with the load transmission lever being abutted against its periphery.

4. The stand according to claim 3, wherein the drive comprises a slide being displaceable relative to the second stand member and having the periphery of the roller abutted against it.

5. The stand according to claim 4, wherein the drive comprises a motor for displacing the slide relative to the second stand member.

6. The stand according to claim 3, wherein the roller comprises a periphery having cogs.

7. The stand according to claim 1, wherein the cam plate comprises a periphery, the distance of which to a center of the cam plate varies in a circumferential direction around the center, with a ratio between a first distance at a first circumferential direction and a second distance at a second circumferential direction being particularly greater than 1.1, and the second circumferential direction forming an angle of more than 20° with the first circumferential direction.

8. The stand according to claim 1, further comprising at least a third stand member being articulated to the first or to the second stand member.

9. A microscopy system comprising:
a microscopy optic; and
a load suspension stand having a plurality of stand members comprising a base stand member and a final stand member supporting the microscopy optic;
wherein the load suspension stand comprises a first stand member; a second stand member; a joint pivotably linking the first stand member to the second stand member; a cam plate rotatably fixed to the first stand member; a load transmission lever; an abutment adapted to pivotably support the load transmission lever at the second stand member; a load reservoir acting on the second stand member and on the load transmission lever in order to exert a force on the cam plate via the load transmission lever; and a drive adapted to displace the abutment relative to the load transmission lever.

10. The microscopy system according to claim 9, further comprising an intermediate lever being pivotably mounted on the second stand member, whereby the load transmission lever transmits the force to the cam plate via the intermediate lever.

11. The microscopy system according to claim 9, wherein the abutment comprises a roller with the load transmission lever being abutted against its periphery.

12. The microscopy system according to claim 11, wherein the drive comprises a slide being displaceable relative to the second stand member and having the periphery of the roller abutted against it.

13. The microscopy system according to claim 12, wherein the drive comprises a motor for displacing the slide relative to the second stand member.

14. The microscopy system according to claim 11, wherein the roller comprises a periphery having cogs.

15. The microscopy system according to claim 9, wherein the cam plate comprises a periphery, the distance of which to a center of the cam plate varies in a circumferential direction around the center, with a ratio between a first distance at a first circumferential direction and a second distance at a second circumferential direction being particularly bigger than 1.1, and the second circumferential direction forming an angle of more than 20° with the first circumferential direction.

16. The microscopy system according to claim 9, further comprising at least a third stand member being articulated to the first or to the second stand member.

* * * * *